(12) United States Patent
Bono et al.

(10) Patent No.: US 9,999,429 B2
(45) Date of Patent: *Jun. 19, 2018

(54) PATIENT-SPECIFIC TOTAL HIP ARTHROPLASTY

(71) Applicant: Howmedica Osteonics Corp., Mahwah, NJ (US)

(72) Inventors: James V. Bono, Dover, MA (US); Stuart L. Axelson, Jr., Succasunna, NJ (US); Adam Bastian, Chester, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/636,194

(22) Filed: Jun. 28, 2017

(65) Prior Publication Data

US 2017/0296206 A1  Oct. 19, 2017

Related U.S. Application Data

(63) Continuation of application No. 15/277,208, filed on Sep. 27, 2016, now Pat. No. 9,717,509, which is a (Continued)

(51) Int. Cl.
   *A61B 17/17* (2006.01)
   *A61F 2/34* (2006.01)
   (Continued)

(52) U.S. Cl.
   CPC .......... *A61B 17/1746* (2013.01); *A61B 34/10* (2016.02); *A61B 90/37* (2016.02);
   (Continued)

(58) Field of Classification Search
   CPC ...... A61F 2/34; A61F 2/4609; A61F 2/30942; A61B 19/50; G06F 19/3437
   See application file for complete search history.

(56) References Cited

U.S. PATENT DOCUMENTS

| 5,037,424 A | 8/1991 | Aboczsky |
| 5,141,512 A | 8/1992 | Farmer et al. |

(Continued)

FOREIGN PATENT DOCUMENTS

| WO | 2010/124164 A1 | 10/2010 |
| WO | 2011/080260 A1 | 7/2011 |

OTHER PUBLICATIONS

International Search Report, PCT/US2011/040869, dated Aug. 22, 2011.

*Primary Examiner* — Christopher Beccia
(74) *Attorney, Agent, or Firm* — Lerner, David, Littenberg, Krumholz & Mentlik, LLP

(57) ABSTRACT

Disclosed herein are systems and methods for performing total hip arthroplasty with patient-specific guides. Pre-operative images of a pelvic region of a patient are taken in order to predefine the structure of the guides and corresponding implants. From the obtained image data an insertional vector for implanting an acetabular implant or component into an acetabulum of the patient is determined, wherein the insertional vector is coaxial with a polar axis of the acetabular component. Also from the obtained image data, a superior surface of the guides and implants can be shaped to match the acetabulum of the patient. A nub portion extending outwardly from the superior surface of the guides and implants is shaped to substantially match the shape of a fovea of the acetabulum. A guide portion of the guides forming a slot has a longitudinal axis coaxial with the determined insertional vector of a corresponding acetabular component.

17 Claims, 18 Drawing Sheets

Related U.S. Application Data continuation of application No. 14/575,403, filed on Dec. 18, 2014, now Pat. No. 9,474,615, which is a continuation of application No. 13/163,037, filed on Jun. 17, 2011, now Pat. No. 8,932,299.

(60) Provisional application No. 61/356,324, filed on Jun. 18, 2010.

(51) Int. Cl.
    *A61B 34/10*     (2016.01)
    *A61F 2/46*     (2006.01)
    *A61B 90/00*     (2016.01)
    *A61B 34/20*     (2016.01)

(52) U.S. Cl.
    CPC .............. *A61F 2/34* (2013.01); *A61F 2/4609* (2013.01); *A61B 34/20* (2016.02); *A61B 2034/104* (2016.02); *A61B 2034/107* (2016.02); *A61B 2034/108* (2016.02); *A61B 2034/2068* (2016.02); *A61B 2090/374* (2016.02); *A61B 2090/376* (2016.02); *A61B 2090/3762* (2016.02); *A61F 2002/3412* (2013.01)

(56) References Cited

U.S. PATENT DOCUMENTS

| | | | |
|---|---|---|---|
| 5,364,403 | A | 11/1994 | Petersen et al. |
| 5,520,694 | A | 5/1996 | Dance et al. |
| 5,611,353 | A | 3/1997 | Dance et al. |
| 5,769,092 | A | 6/1998 | Williamson, Jr. |
| 5,769,856 | A | 6/1998 | Dong et al. |
| 6,395,005 | B1 | 5/2002 | Lovell |
| 6,676,706 | B1 | 1/2004 | Mears et al. |
| 6,935,480 | B2 | 8/2005 | Ziemer |
| 6,991,656 | B2 | 1/2006 | Mears |
| 7,547,307 | B2 | 6/2009 | Carson et al. |
| 7,651,501 | B2 * | 1/2010 | Penenberg ......... A61B 17/1746 606/91 |
| 7,927,338 | B2 | 4/2011 | Laffargue et al. |
| 8,133,234 | B2 | 3/2012 | Meridew et al. |
| 8,177,850 | B2 | 5/2012 | Rudan et al. |
| 8,206,396 | B2 | 6/2012 | Trabish |
| 2005/0065617 | A1 | 3/2005 | Moctezuma de la Barrera et al. |
| 2005/0148843 | A1 | 7/2005 | Roose |
| 2005/0234461 | A1 | 10/2005 | Burdulis et al. |
| 2007/0198022 | A1 | 8/2007 | Lang et al. |
| 2008/0009952 | A1 | 1/2008 | Hodge |
| 2008/0033430 | A1 | 2/2008 | Ferrante et al. |
| 2008/0033442 | A1 | 2/2008 | Amiot et al. |
| 2008/0269757 | A1 | 10/2008 | McMinn |
| 2008/0281329 | A1 * | 11/2008 | Fitz ...................... A61B 5/4528 606/88 |
| 2008/0287954 | A1 | 11/2008 | Kunz et al. |
| 2008/0312663 | A1 | 12/2008 | Haimerl et al. |
| 2009/0149965 | A1 | 6/2009 | Quaid |
| 2009/0163922 | A1 | 6/2009 | Meridew et al. |
| 2009/0163923 | A1 | 6/2009 | Flett et al. |
| 2009/0192620 | A1 | 7/2009 | Ebbitt |
| 2009/0222016 | A1 | 9/2009 | Park et al. |
| 2009/0254093 | A1 | 10/2009 | White et al. |
| 2010/0016984 | A1 | 1/2010 | Trabish |
| 2010/0016986 | A1 | 1/2010 | Trabish |
| 2010/0082035 | A1 | 4/2010 | Keefer |
| 2010/0274253 | A1 * | 10/2010 | Ure ................... A61B 17/1746 606/91 |
| 2010/0286700 | A1 | 11/2010 | Snider et al. |
| 2011/0015636 | A1 | 1/2011 | Katrana et al. |
| 2011/0015637 | A1 | 1/2011 | De Smedt et al. |
| 2011/0015639 | A1 | 1/2011 | Metzger et al. |
| 2011/0024583 | A1 | 2/2011 | Hoernig |
| 2011/0093086 | A1 | 4/2011 | Witt et al. |
| 2011/0160867 | A1 | 6/2011 | Meridew et al. |
| 2011/0184419 | A1 | 7/2011 | Meridew et al. |
| 2011/0224674 | A1 | 9/2011 | White et al. |
| 2011/0306978 | A1 | 12/2011 | Ries et al. |
| 2011/0313423 | A1 | 12/2011 | Lang et al. |
| 2011/0313424 | A1 | 12/2011 | Bono et al. |
| 2012/0041445 | A1 | 2/2012 | Roose et al. |
| 2012/0078258 | A1 | 3/2012 | Lo et al. |
| 2012/0078259 | A1 | 3/2012 | Meridew |
| 2012/0109137 | A1 | 5/2012 | Iannotti et al. |
| 2012/0109138 | A1 | 5/2012 | Meridew et al. |
| 2012/0123420 | A1 | 5/2012 | Honiball |
| 2012/0123423 | A1 | 5/2012 | Fryman |
| 2012/0141034 | A1 | 6/2012 | Iannotti et al. |
| 2012/0143267 | A1 | 6/2012 | Iannotti et al. |
| 2012/0165820 | A1 | 6/2012 | De Smedt et al. |
| 2012/0172884 | A1 | 7/2012 | Zheng et al. |
| 2012/0226283 | A1 | 9/2012 | Meridew et al. |
| 2012/0230573 | A1 | 9/2012 | Ito et al. |
| 2012/0265208 | A1 | 10/2012 | Smith |

* cited by examiner

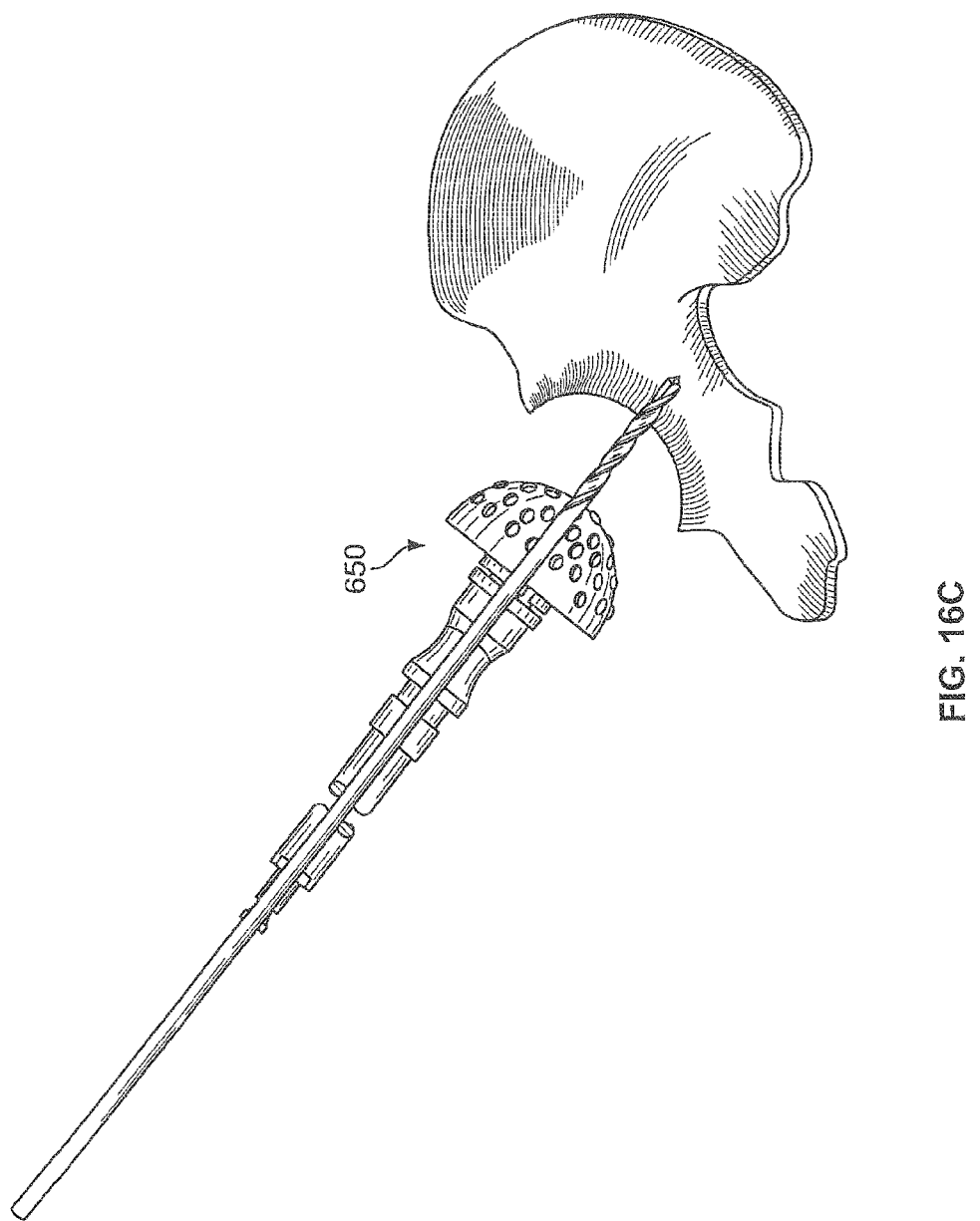

PATIENT-SPECIFIC TOTAL HIP ARTHROPLASTY

CROSS REFERENCE TO RELATED APPLICATIONS

The present application is a continuation of U.S. patent application Ser. No. 15/277,208 filed Sep. 27, 2016, which is a continuation of U.S. patent application Ser. No. 14/575,403 filed Dec. 18, 2014, now U.S. Pat. No. 9,474,615, which is a continuation of U.S. application Ser. No. 13/163,037 filed Jun. 17, 2011, now U.S. Pat. No. 8,932,299, which claims the benefit of the filing date of U.S. Provisional Patent Application No. 61/356,324 filed Jun. 18, 2010, the disclosures of which are hereby incorporated herein by reference.

BACKGROUND OF THE INVENTION

The present invention relates to providing instruments for the alignment of an acetabular cup within the acetabulum, which may include preoperative imaging to create a patient-specific guide for predefining the resection of the acetabulum to receive the acetabular cup.

The success of hip joint replacement surgery, which is a well-accepted treatment for arthritic conditions of the hip, depends upon preoperative planning and also the proper intraoperative placement of reamers, alignment instruments, and implants, for example, in order for the function of the joint to be optimized biologically and biomechanically. In particular, in hip replacement surgery, successful hip reconstruction is predicated upon restoring the biomechanics of the hip to "normal," as well as selecting implants of appropriate size to avoid intraoperative or postoperative complications and to ensure long-lasting function.

The hip is a ball and socket joint. In the normal hip, the femoral head is generally circular and rotates within the acetabulum which is also generally circular. Ideally, the stress transfer of body weight across the hip joint is distributed across the surface area of the femoral head and acetabulum. A distribution of stress generally results in lower stresses in the joint, as the maximum amount of surface area is being used to distribute the stress.

In the diseased hip, the ball and socket may be malformed, and may result in an abnormally uneven distribution of stress. A deformed femoral head, for example, one that is generally more oblong than circular, will transfer stress from the femoral head to the acetabulum along the periphery of the femoral head to the periphery of the acetabulum. This transfers the entire amount of stress, imported by the body weight, to a much reduced surface area, thereby increasing the stress per unit area. The resulting increased stress per unit area generally damages the joint by damaging the articular cartilage, which, may wear out.

From a biomechanical standpoint, successful hip function depends on proper orientation of the muscles in relation to the center of rotation of the joint, such that leg length and offset are equalized following surgery. Surgery may be performed to restore the length of the leg to its original length, which in turn aims to restore the original biomechanics of the joint and thereby optimize function. A preoperative determination of the precise amount of the leg-length discrepancy, if any, is necessary to correct the discrepancy intraoperatively and achieve leg-length equality, in other words, avoid over-lengthening or under-lengthening of the leg.

In addition, restoration of hip function by performance of hip replacement surgery depends upon reproduction of the femoral offset. The femoral offset is the distance from the center of rotation of the hip joint to the longitudinal axis of the femoral shaft. The accurate determination of the femoral offset is important, because the femoral offset determines the moment arm of the abductor muscles, in other words, how hard the muscles have to work. Therefore, in a surgical hip replacement procedure, the offset needs to be restored appropriately for the hip to function properly. If a hip prosthesis is installed with insufficient offset because an acetabular component, for example, an acetabular cup, has not been properly positioned in the acetabulum, the hip muscles will have to generate increased force, which may lead to discomfort and easy fatigability.

Alignment of an acetabular cup can be achieved with an alignment guide that attaches to an insertion rod for facilitating the insertion of the acetabular cup into the acetabulum. The alignment guide preferably references the surgical table on which the patient rests. Conventionally, it is assumed that the patient's pelvis is parallel to the table, and that the surgical table is parallel to the floor. Based on such assumptions, the ordinary position (in most patients) for the acetabular cup is 45° of inclination and 20° of anteversion. For a discussion of angles of anteversion and also inclination or abduction of the acetabular cup when installed in the acetabulum, see, for example, U.S. Pat. No. 6,395,005, which is incorporated by reference herein in its entirety and is fully set forth herein.

It is has been found based on post-operative x-rays, however, that despite the alignment guide being parallel to the floor during insertion of the acetabular cup, the resultant inclination or anteversion of the acetabulum in relation to the alignment guide is often different than expected and, thus, the acetabular cup has been installed at a less than ideal position. In some circumstances, the inaccurate positioning of the acetabular cup may be caused by tilting of the pelvis of the patient in the lateral decubitus position during the surgical procedure, which titling is not recognized during the procedure.

Some surgeons use intraoperative x-rays and navigation for detecting pelvic tilt intraoperatively. Intraoperative x-ray, however, is often time consuming and can potentially increase the risk of infection due to the introduction of x-ray equipment into the operating theater. The X-ray image, which is taken through the anterior/posterior (AP) view of the pelvis, typically is of poor quality and bony landmarks are often obscured, which makes accurate measurement of the pelvic tilt difficult. Also, although intraoperative x-rays may used to determine pelvic tilt, which in turn allows for a determination of the proper inclination of the acetabular component, the x-rays cannot provide information from which the proper anteversion of the acetabular component can be determined.

In light of the above, there remains a need for a straightforward method and system for the precise positioning of components relative to the acetabulum.

BRIEF SUMMARY OF THE INVENTION

In accordance with one aspect of the present invention is a patient-specific guide used in hip arthroplasty and a method of creating such a patient-specific guide. Preoperative images of a patient's pelvic region are used in determining a patient-specific contact surface of the guide. The contact surface substantially matches the shape of at least a portion of the acetabulum such that the guide is stable once it is engaged to the acetabulum. The outer surface of the acetabulum whether bone and/or cartilage that the contact surface of the guide is configured to engage is thus a negative of the contact surface of the guide.

With respect to the present aspect, the guide is generally used in hip arthroplasty procedures for patients with a deformed acetabulum due to bone degeneration and/or wear, for example. Instead of a generally circular configuration, the deformed acetabulum is generally ovular. Even though the contact surface of the guide is patient-specific, it may still be difficult to orient the guide in a correct preoperatively planned location because of the ovular configuration of the deformed acetabulum. Even if the guide is rotated in either a clockwise or counterclockwise orientation while adjacent to the acetabulum, the guide will not necessarily key into the correct preoperatively planned location.

In accordance with the present aspect, the fovea of the acetabulum is preferably used as an anatomical landmark to easily orient the guide in the correct preoperatively planned position. Information relating to the location, size and shape of the fovea is analyzed in the preoperative images taken of the acetabulum. This information is used in order to create the patient-specific contact surface of the guide having a feature such as a protrusion on the contact surface of the guide representing the negative of the fovea.

The fovea is an anatomical landmark that is unique to each patient. The fovea is a recess or depression located generally at the bottom of the acetabulum. The fovea is generally shaped like an oval or horseshoe and is approximately one centimeter deep. The fovea is generally located along a portion of the periphery of the acetabulum and extends approximately one-third of the acetabular floor toward the superior apex of the acetabulum. Because the fovea is shaped and located uniquely in every individual, there are no two individuals who have identically shaped fovea in the same location relative to the deformed acetabulum.

In accordance with the present aspect, the guide further includes a guide slot. Preoperative images of a patient's pelvic region are also used in determining the location and orientation of the guide slot of the guide. The guide slot has an axis representing an insertional vector of an acetabular component. During the preoperative planning of the guide, accurate acetabular component placement is generally first determined. The polar axis of the acetabular component in the accurately placed or implanted location and orientation is preferably co-linear with the axis of the guide slot.

Once the optimal location of the acetabular component is determined in order, for example, to correct a patient's deformity, the location and orientation of the guide slot of the guide may then be determined. The guide slot of the guide is adapted to receive means for resecting bone. The bone resection means may be a rotating drill, for example. Once the guide is correctly positioned, a drill may be used to resect a portion of bone and/or cartilage of the acetabulum. After a portion of the bone and/or cartilage of the acetabulum is removed, the guide may then be removed. A guide recess formed by the resection, the recess having an axis co-linear with the polar axis of a correctly placed acetabular component is now located in the bone of the acetabulum. This guide recess is used to accurately locate a cutting tool such as a reamer, for example, used to remove a sufficient amount of the bone of the acetabulum in order to repair the contact surface for the acetabular component that will be engaged thereto. After the acetabulum is reamed, the acetabular component is accurately implanted in the acetabulum and affixed thereto with a fastening means such as a screw, for example. The screw is positioned through a hole in the acetabular component and into the guide recess previously formed by the guide slot of the guide. A longitudinal axis of the hole is co-linear with the polar axis of the accurately positioned acetabular component.

Another aspect of the present invention is a method of performing a preoperative plan for implanting a patient-specific acetabular implant. The method includes using three-dimensional ("3D") imaging data of a pelvic region of a patient. The image data is used to determine an insertional vector for inserting an acetabular implant into an acetabulum of a hip of the patient, wherein the insertional vector extends through a center of rotation of the hip of the patient. The method further includes constructing a 3D model of the acetabular implant in relation to the insertional vector and the center of rotation of the hip, wherein the 3D model of the acetabular implant includes a superior surface opposing the acetabulum and is shaped to substantially match the shape of the acetabulum, wherein the superior surface defines a nub portion or protrusion shaped to substantially match the shape of the fovea of the acetabulum. The nub portion is positioned and oriented on the superior surface such that, when the acetabular implant obtained from the 3D model is inserted into the acetabulum of the hip of the patient with a center of rotation of the acetabular implant aligned with the insertional vector, the nub portion can be received substantially directly in the fovea of the acetabulum.

In one embodiment of the present aspect, the method further includes using topographical landmarks of the pelvic region of the patient included in the 3D imaging data of the pelvic region to determine the center of rotation of the hip, and an anteversion angle and an abduction angle from which the insertional vector is determined.

In another embodiment of the present aspect, the constructing of the 3D model of the acetabular implant includes using digital subtraction to shape the 3D model of the acetabular implant in relation to a contour of the acetabulum and the fovea.

In yet another embodiment of the present aspect, the method further includes using the 3D imaging data to determine the center of rotation of the hip by positioning a digitized representation of a sphere substantially centered within the acetabulum and sized for substantially contacting each of superior, inferior, anterior and posterior quadrants of the acetabulum.

In yet still another embodiment of the present aspect, the sphere has a medial border disposed midway between an inner wall and an outer wall of the pelvis.

Another aspect of the present invention is a patient-specific acetabular implant for insertion into an acetabulum of a hip of a patient. The acetabular implant is obtained using a 3D model of the acetabular implant and 3D imaging data of the pelvic region of the patient. The image data is used to determine an insertional vector for inserting the acetabular implant into the acetabulum of the hip of the patient, wherein the insertional vector extends through a center of rotation of the hip of the patient. The image data is further used to construct the 3D model of the acetabular implant in relation to the insertional vector and the center of rotation of the hip, wherein the acetabular implant includes a superior surface to oppose the acetabulum and shaped to substantially match the shape of the acetabulum. The superior surface defines a protrusion or nub portion shaped to substantially match the shape of the fovea of the acetabulum, wherein the nub portion is positioned and oriented on the superior surface such that, when the acetabular implant obtained from the 3D model is inserted into the acetabulum of the hip of the patient with a center of rotation of the acetabular implant aligned with the insertional vector, the nub portion can be received substantially directly in the fovea of the acetabulum.

In one embodiment of the present aspect, topographical landmarks of the pelvic region of the patient included in the 3D imaging data of the pelvic region are used to determine the center of rotation of the hip, and an anteversion angle and an abduction angle from which the insertional vector is determined.

In yet another embodiment of the present aspect, the 3D model of the acetabular implant is constructed using digital subtraction to shape the 3D model of the acetabular implant in relation to a contour of the acetabulum and the fovea.

In yet still another embodiment of the present aspect, the center of rotation of the hip is determined using the 3D imaging data by positioning a digitized representation of a sphere substantially centered within the acetabulum and sized for substantially contacting each of a superior, inferior, anterior and posterior quadrants of the acetabulum.

In yet still another embodiment of the present aspect, the sphere has a medial border disposed midway between an inner wall and an outer wall of the pelvis.

Another aspect of the present invention is a method of using a patient-specific guide in conjunction with a navigation system for preparation and positioning of an acetabular component. Preoperative images of a patient's pelvic region are taken using computer tomography ("CT"), magnetic resonance imaging ("MRI"), or other imaging methodology. The images are evaluated to determine the correct axis of orientation for the acetabular cup to achieve optimal range of motion for a femoral component and maximum acetabular body coverage while minimizing the reaction forces experienced in the acetabular cup. The image data is manipulated to create a patient-specific 3D model guide depicting the unique negative impression of the contour of the acetabulum with a guide slot having an axis incorporated as a feature in the model. The patient-specific guide may then be manufactured.

Intraoperatively, a patient is prepared in a standard manner for a navigated total hip arthroplasty procedure. Tracker pins may be placed in the iliac crest or other rigid area of the acetabulum. Incision is made and the femoral neck is resected. The patient-specific guide is then placed into the acetabulum. A navigated pointer may be inserted into the guide slot or may alternatively be aligned with the prescribed axis. The navigation system preferably registers the exact orientation and location including depth of the pointer relative to a global coordinate system created by the trackers. The patient-specific guide may then be removed from the acetabulum. A navigated reamer handle and then navigated cup inserter are used to prepare the acetabulum in the correct orientation based on the registered target.

BRIEF DESCRIPTION OF THE DRAWINGS

Other objects and advantages of the present invention will be apparent from the following detailed description of the present preferred embodiments, which description should be considered in conjunction with the accompanying drawings in which like reference indicate similar elements and in which:

FIG. 16C is a view of the guide pin shown in FIG. 16B guide the direction of a cannulated reamer.

DETAILED DESCRIPTION

Figure 1:
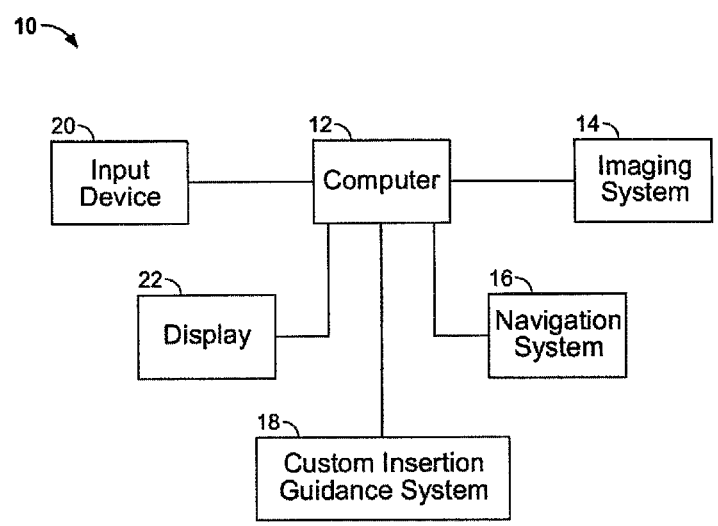
FIG. 1 is a block diagram of a system in accordance with an aspect of the present invention.

FIG. 1 is a block diagram of a surgical guidance system 10, in accordance with the present invention. Referring to FIG. 1, the system 10 includes a computer 12 coupled to an imaging system 14, a navigation system 16 and an instrumentation guidance system 18. The system 10 further includes an input device 20 and a display 22.

The imaging system 14 is a conventional imaging device for providing medical images, such as X-rays, fluoroscopic, CT, MRI, etc., of a patient's anatomical regions.

The navigation system 16 is a conventional device including positional sensors or trackers for attachment to a patient and surgical instruments for reporting the location and orientation of the patient's anatomy and a surgical instrument in 3D space.

The computer 12 is a conventional processor including a memory and capable of exchanging data and control signals with the imaging system 14 and the navigation system 16 for obtaining images of the patient, and for tracking data representative of the location and orientation of the patient and surgical instruments in 3D space, respectively. See U.S. Patent Application Publication No. 2005/0203384, incorporated by reference herein.

The display 22 is a conventional device for displaying images obtained by the imaging system 14, and virtual representations of a portion of the patient and a surgical or implant instrument in 3D space on an image of the patent, where the virtual representations are based on data obtained from the navigation system 16 or operation of the guidance system 18, in accordance with the present invention as discussed in detail below.

The input device 20 is a conventional data entry device, such as a keyboard, mouse, voice recognition system, etc. through which a user can input data for performing operations related to determining a preoperative plan through use of the guidance system 18.

The guidance system 18, as discussed in detail below, includes a processor containing a memory and performs data processing operations for defining a preoperative plan for a surgical procedure in the pelvic region of a patient using imaging data obtained by the imaging system, and for implementing the pre-operative plan in a surgical procedure using tracking data obtained from the navigation system 16.

Figure 2:
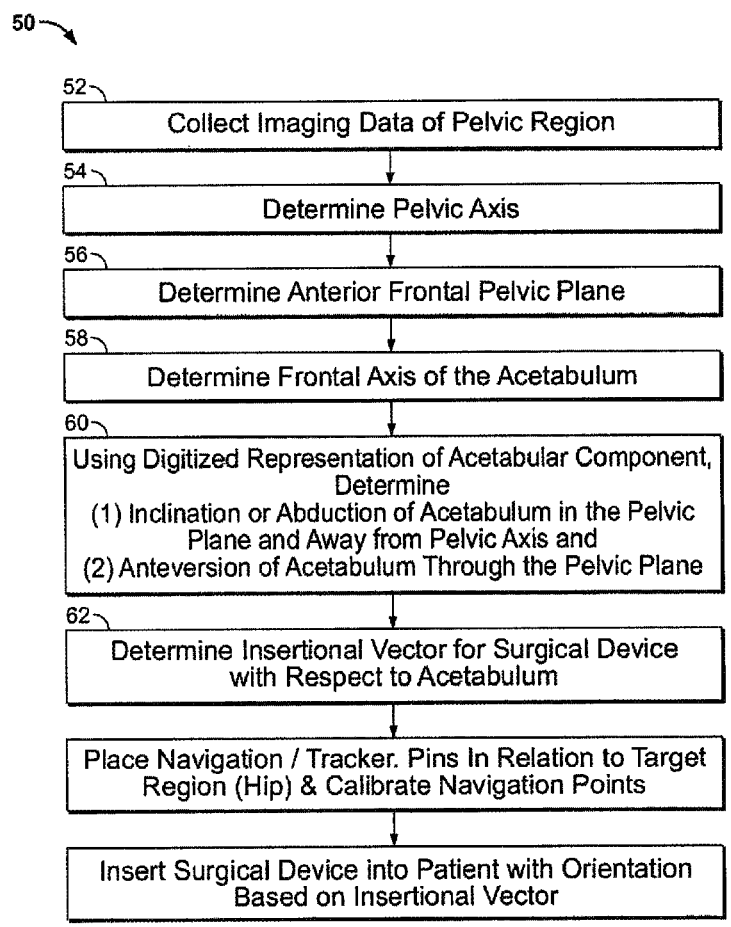
FIG. 2 is a flow diagram of a process in accordance with an aspect of the present invention.

FIG. 2 is an exemplary process 50 for determining, based on images of the pelvic region of a patient, an insertional vector which can be used to create a guide slot for a patient-specific acetabular guide or for the positioning of a surgical instrument such as a navigated pointer during a surgical procedure, in accordance with the present invention. As discussed below, the insertional vector determined from the process 50 can be used to preoperatively plan a surgery in the pelvic region, such as a hip joint replacement surgery procedure, such that potential complications can be identified and planned, and to increase the overall accuracy of the surgically invasive operations, thereby reducing the potential for intraoperative complications. The use of the insertional vector intraoperatively assures accurate execution of the preoperative plan.

For purposes of illustration, the process 50 is exemplified for determining an insertional vector for use in a total hip replacement, using a 3D reference coordinate system defined by X, Y, and Z axes, where a user interacts with the guidance system 18 via the input device 20 and display 22 to define the reference coordinate system using images of the pelvic region of a patient obtained, such as by the imaging system 15.

Figure 3:
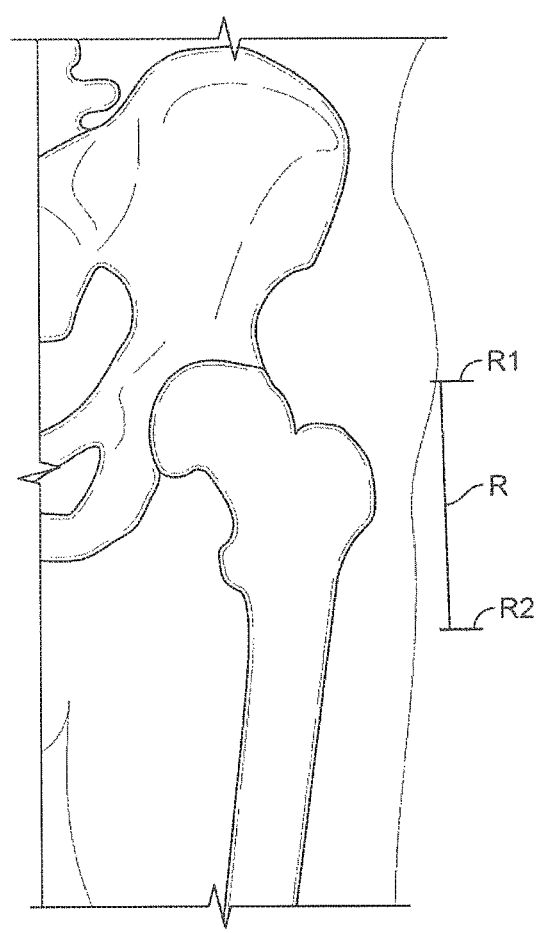
FIG. 3 is an image of a portion of the pelvic region.

Referring to FIG. 2, in block 52, the imaging system 14 may obtain images of the patient's pelvic region and forward the image data to the computer 12, where the image data is stored in memory. In one embodiment, the images are two-dimensional images, such as a radiograph. For example, x-rays are taken of the pelvic region, where the pelvic region contains an existing implant of a known dimension. Alternatively, an x-ray of the pelvic region includes a radiographic marker of known dimension that has been affixed adjacent to the pelvic region, external to the patient. Referring to FIG. 3, a radiographic marker element R having a known dimension between marker metal beads R1 and R2 can be taped to the skin of the patient at the level of the trochanter.

In one embodiment, the guidance system 18 retrieves the x-ray image data from the computer 12 and processes such image data, based on the known dimensions of an object included in an image, for example, based on the known distance between the beads R1 and R2 as shown in FIG. 3, to determine whether the x-ray images have any magnification. The amount of magnification, if any, is stored in memory in the guidance system 18, and then used to correct for measurements made in other steps of the process 50 as discussed below. Thus, all measurements of distances between objects in the images of the pelvic region processed as part of the process 50 are neither increased nor decreased artificially.

In an alternative embodiment, the imaging system 14 in block 52 obtains 3D images of the pelvic region, which do not have any magnification, and forwards such images to the computer 12.

In block 52, the guidance system 18 receives data representative of the coordinate reference system the imaging system 14 used when the images were obtained, which the imaging system 14 provided to the computer 12 for use by the guidance system 18. The imaging coordinate reference system data provides the guidance-related reference coordinates, which correspond to the locations of lines or points on a collected image that may be generated by use of the guidance system 18. This data can be correlated to locations on a second collected image and provide the corresponding lines or points on the second image which would be determinable and can be displayed on the second image at a corresponding location(s). For example, based on input received from the user at the input device 20, a selected image of the pelvic region is displayed on the display 22, and the guidance system 18 displays markings and axial lines, which are based on user inputs or the guidance system 18 generates, superimposed on the displayed image.

Figure 4A:
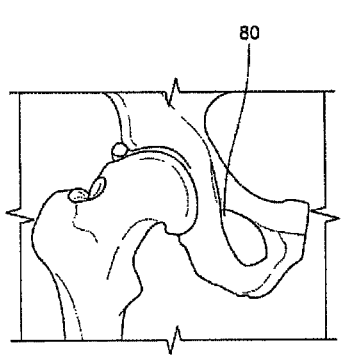
FIG. 4A is an image of a portion of the pelvic region including an anatomical landmark.
Figure 4B:
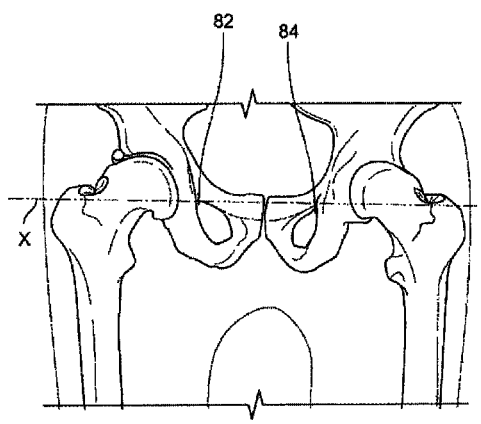
FIG. 4B is an image of the pelvic region including a pelvic axis.

In block 54, the user operates the guidance system 18 to identify a pelvic axis (or X axis) and its orientation in the subject pelvic region. The pelvic axis corresponds to an X axis as shown in FIG. 4B of a guidance reference system, which can be used to determine an insertional vector for performing a surgical procedure at the pelvic region. The determination of the orientation of the pelvic axis for the pelvic region provides useful information for properly positioning a surgical instrument during a pelvic region surgical procedure because, oftentimes, the pelvis of a patient may be rotated or tilted during such a procedure. In addition, the pelvic axis may be used as a reference point for measuring the length of a leg of the patient.

In one embodiment of the block 54, the user selects a collected 2D image of the pelvic region for display and identifies with digital markings on the image, such as by clicking a mouse, corresponding anatomical landmarks on the left and right hips of the patient. For example, the landmarks may include the acetabular teardrop 80 as shown in FIG. 4A, the ischial tuberosity the obturator foramen, or the greater sciatic notch. When the displayed image is a conventional radiograph, a desired and commonly used landmark is the acetabular teardrop ("TD"), which is commonly visible on an image of an anteroposterior view of the pelvic region as shown in FIG. 4A. Referring to FIG. 4B, the user digitally marks the left ("Left TD") and right ("Right TD") acetabular teardrops 82, 84 of the pelvic region on the image. The guidance system 18 then automatically inserts onto the image a line extending through the Left TD and Right TD markings, and such line corresponds to the pelvic axis or X-axis of a reference coordinate system to be used in pre-operative planning. As discussed below, the pelvic axis can be used to determine the appropriate abduction or inclination angle of an acetabular component, such as the acetabular cup, with respect to a coordinate reference system, to provide acetubular components, such as included in a complete hip prosthesis, and desirably an acetabular cup, may be properly and accurately positioned in the pelvic region of a patient.

Figure 5A:
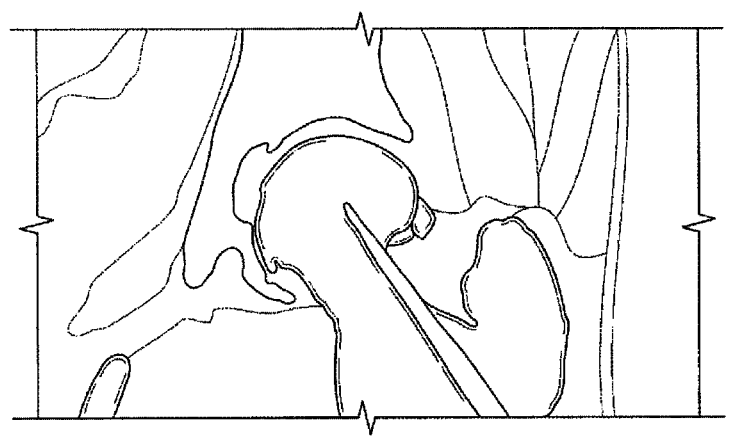
FIGS. 5A and 5B are images of a portion of the pelvic region including a virtual representation of an acetabular component.
Figure 5B:
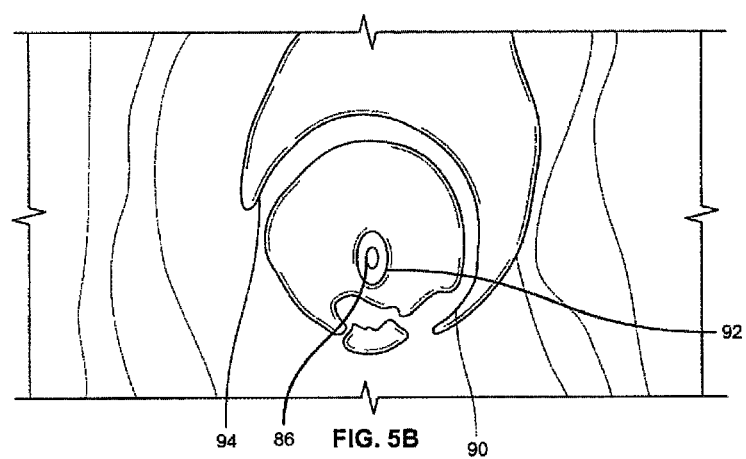

In an alternative embodiment, 3D images may be used to define the pelvic axis (X axis) in block 54. Referring to FIGS. 5A and 5B, the user, via the guidance system 18, selects an image displayed on the display containing the acetabulum region of a hip joint of the patient. After the image is selected, the user operates the guidance system 18 to generate digitally a virtual representation of a sphere 86 on the image. The user, with the input device 22, adjusts the size and position of the virtual sphere, so as to superimpose the virtual sphere generally within the confines of the acetabulum of one of the hips. The user then further adjusts the position of the virtual sphere to position the sphere centrally within the acetabulum, and the size of the sphere so that its outer surface touches the edge of all quadrants, e.g., superior, inferior, anterior, and posterior of the acetabulum, and the medial border 90 of the sphere is positioned midway between the inner and outer walls 92, 94 of the pelvis.

Figure 6A:
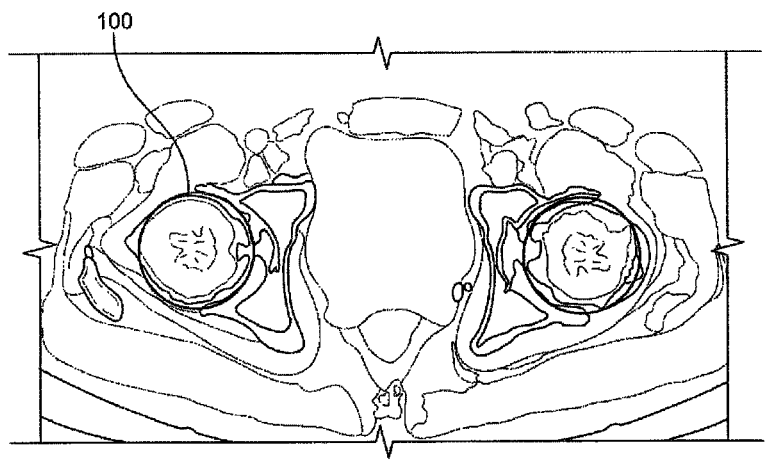
FIG. 6A is an image of a portion of the pelvic region including virtual representations of acetabular components positioned in relation to the left and right acetabulums, respectively.
Figure 6B:
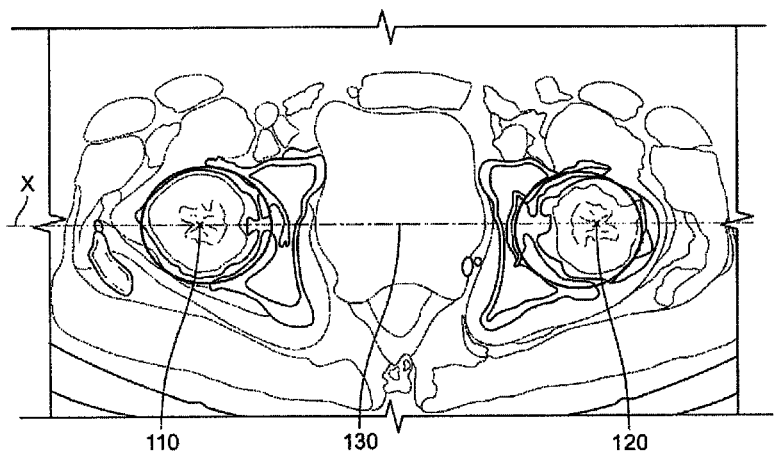
FIG. 6B is the image of FIG. 6A including a pelvic axis.

The user positions a virtual digital sphere 100 within the acetabulum for each of the hips on the image, as shown in FIG. 6A. When the virtual spheres 100 have been appropriately sized and positioned within the acetabulums for the respective hips, the center of each of the spheres 110, 120 corresponds to the center of rotation for the hip. After placement of the virtual spheres 100 at the desired position within the acetabulums, the user enters an instruction at the input device 20, which indicates to the guidance system 18 that the sizing and the positioning of the spheres has been completed. After the guidance system receives such indication, the guidance system 18 automatically generates on the image a line 130 extending through the centers Center-R 110 and Center-L 120 of the virtual spheres 100 at the left and right hips, respectively, as shown in FIG. 6B, and such line 130 constitutes the pelvic axis (X axis) of the pelvic region.

Figure 7:
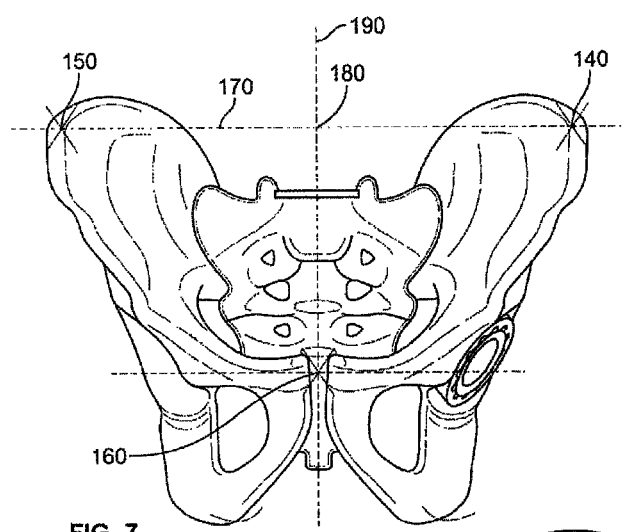
FIG. 7 is an image of a portion of the pelvic region including anatomical points in the anterior frontal plane of the acetabulum.

In block 56, the user selects from the images collected by the imaging system 14 an image of the pelvic region from which the anterior frontal pelvic plane of the patient can be determined. Referring to FIG. 7, after the user selects an image, such as by providing a suitable indication using the input device 20, the guidance system 18 may automatically insert onto the selected image the pelvic axis previously determined in block 54, at the corresponding location. The user, using a mouse, digitally marks on the image reference points corresponding to the left and right anterior superior iliac spines ("Left ASIS" 140 and Right ASIS" 150) and the pubic symphysis ("PS") 160. After such points are digitally marked, the system 18 determines the points of a plane containing these three reference points, and stores in its memory information representative of the points of the plane for the image in relation to the image reference system. Such plane constitutes the anterior frontal plane of the acetabulum for the left and right hips.

In block 58, based on the anterior plane data stored in memory, the guidance system 18 determines, and optionally displays on the image on which the anterior plane was defined, the coordinates of a line ("ASIS line") 170 connecting the Right ASIS to the Left ASIS, and then determines the coordinates of a point ("MP") 180 on the ASIS line corresponding to the midpoint. Further, the guidance system 18 determines the coordinates of an axial line 190 extending through the reference point PS and the point MP, and optionally displays the line on the image. Such axial line lies in the anterior plane and constitutes the Y-axis of the guidance coordinate reference system. The Y-axis corresponds to the frontal axis of the acetabulums of the left and right hips of the patient.

In block 60, the orientation of the acetabulum of a hip on which a surgical procedure is to be performed, in relation to the frontal axis, the pelvic axis and the pelvic plane of the pelvic region of the patient, is determined. Based on the orientation determination, the orientation of a surgical instrument used in the surgical procedure for hip replacement, and also of an acetabular component to be inserted into or in relation to the acetabulum, can be determined, to provide for precision placement or movement of a surgical instrument or device during the surgery. In one embodiment, the orientation of an acetabular cup, which is to be positioned within the acetabulum as part of a hip replacement surgical procedure, is determined with respect to the reference axes and plane of the guidance coordinate system. The orientation of the acetabular cup to be determined includes (i) inclination or abduction and (ii) anteversion.

To determine the inclination or abduction, the guidance system 18 digitally generates a representation of an acetabular cup for one of the hips, for example, the left hip. The center of the cup is positioned initially along the pelvic axis at the same location as the center of the digital sphere for the left hip from which the pelvic axis was defined. For ease of understanding, it is assumed that the virtual cup includes a flat, circular surface and the surface is displayed initially co-planar with the anterior plane, with the center of the cup positioned on the pelvic axis at the same location as the center of rotation of the virtual sphere for the left hip. The user, using the input device 20, rotates the cup about its center, away from the pelvic axis and in the frontal plane, to determine an angle of inclination or abduction. The user observes the rotation of the cup on the display and continues to provide for rotation of the virtual cup until the inclination corresponds to the inclination of the acetabulum for the left hip as shown on the image. The angle of rotation of virtual cup away from the pelvic axis is the angle of inclination, and the guidance system 18 stores such information in its memory.

In one embodiment, after the guidance system 18 positions the virtual acetabular cup in relation to the pelvic axis with the center of the virtual cup at the same point as the center of digital sphere for the acetabulum in which the cup is to be installed, the guidance system 18 rotates the cup 45 degrees with respect to the pelvic axis and about its center of rotation, and then displays the virtual cup on the image with such inclination.

Figure 8:
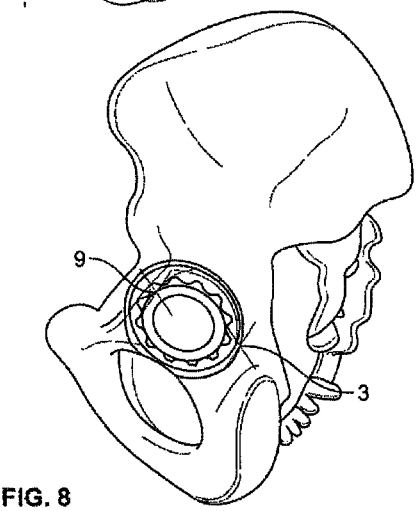
FIG. 8 is an image of a portion of the pelvic region for determining anteversion of the acetabular component.

Further in block 60, the anteversion of the acetabular component is determined. In one embodiment, the user selects another image of the acetabulum of the left hip for display. After the user selects the image, the user, with the input device, digitally marks reference points on the acetabulum for use in determining the anteversion. For example, the reference points are the bone landmarks of the edge of the anterior and posterior wall of the acetabulum, which correspond to the 3 o'clock and 9 o'clock position of the acetabulum. The user digitally marks such reference points "3" and "9" on the image as shown in FIG. 8. The navigation system 16 provides that the user, using the input device 20, can cause the virtual cup to rotate about an axial line ("Inclination/Abduction axis") extending in the frontal plane and passing through the center of rotation of the cup. Such rotation of the virtual cup corresponds to rotation in an anterior direction or with respect to the Z axis of the guidance coordinate reference plane, so that the edge of the virtual cup is tangent to the two points "3" and "9", as shown in FIG. 8.

In one embodiment, the guidance system 16 automatically rotates the virtual cup about the inclination/abduction axis 20 degrees, and stores information representative of such rotation in memory.

In block 62, the guidance system 16 determines the insertional angle or vector for a surgical instrument or surgical device, such as an acetabular component, based on the coordinate reference system defined in blocks using the pelvic and frontal axes and the frontal plane, and the data representative of the inclination/abduction and anteversion of the acetabulum for such reference system, is determined.

The insertional vector is then used in preparing a preoperative plan. In one embodiment, the insertional vector is used to define a guide slot in a patient-specific guide in order to accurately position an acetabular component, such as an acetabular cup, to be inserted into the acetabulum. The guide slot has an axis that is angled to correspond to the insertional vector, and in particular has determined the correct location and position of the acetabular component (using the pelvic and frontal axes as references). As every patient's anatomy is unique to them, a custom mold of the patient's acetabular cavity will "key" into position in vivo. The mold will include an alignment reference which will recapitulate the preoperative plan. During final insertion of the prosthesis, the surgeon will reference the orientation of the shape fitting mold to assure accurate inclination and anteversion of the prosthetic component. In doing so, acetabular component alignment errors due to pelvic tilt and rotation during surgery will be eliminated.

The patient-specific total hip replacement insertional device is then created to mimic this insertional vector in vivo using topographical landmarks unique to the patient. Using digital subtraction, the 3D image removes the femoral head and traces the contour of the patient's acetabular bed, including the fovea. At the conclusion of steps one through seven, appropriate cup size, location, inclination, and anteversion will be determined. This is necessary in order to reestablish proper acetabular component position which is a prerequisite for successful prosthetic reconstruction of the joint.

Figure 9:
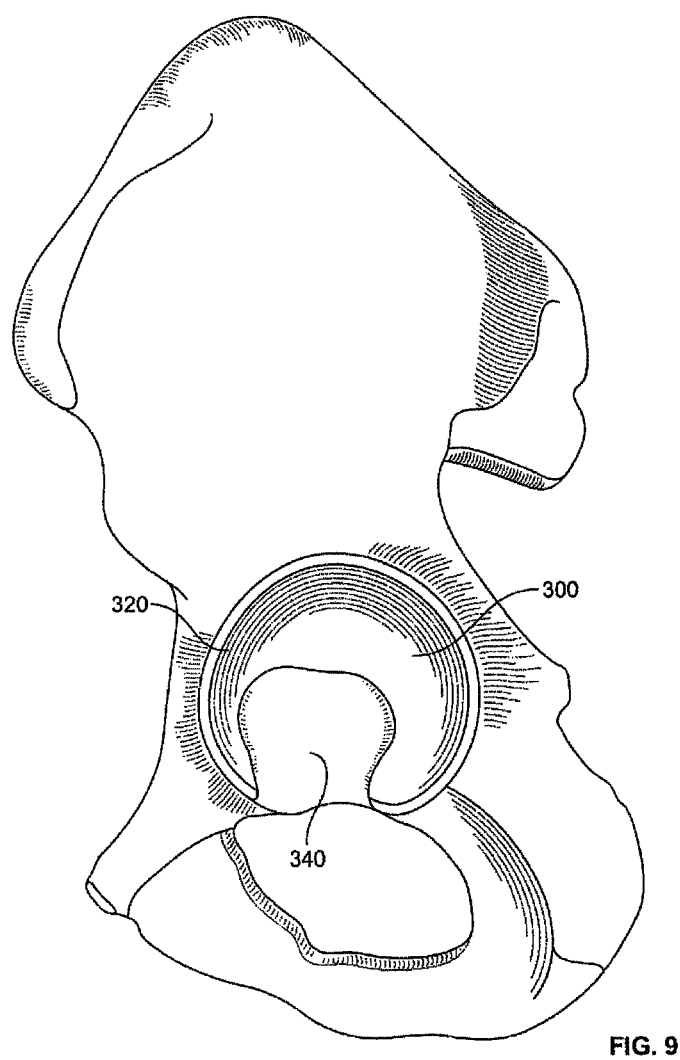
FIG. 9 is a view of the right-side of a patient's pelvic region.
Figure 10:
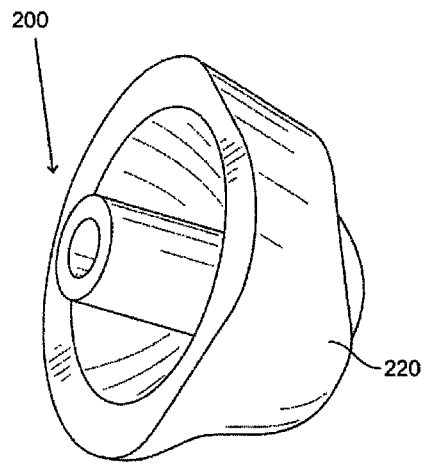
FIG. 10 is a perspective view of a patient-specific guide of the present invention.

In one embodiment, preoperative images of a patient's pelvic region as shown in FIG. 9 are used in determining a patient-specific contact surface 220 of guide 200 as shown in FIG. 10. The contact surface 220 substantially matches the shape of at least a portion of the acetabulum 300 such that the guide 200 is stable once it is engaged to the acetabulum 300. The outer or articular surface 320 of the acetabulum whether bone and/or cartilage that the superior or contact surface 220 of the guide 200 is configured to engage is thus a negative of the contact surface 200 of the guide 200.

Guide 200 is generally used in hip arthroplasty procedures for patients with a deformed acetabulum due to bone degeneration and/or wear. Instead of a generally circular configuration, the deformed acetabulum is generally ovular. Even though the contact surface 220 of guide 200 is patient-specific, it is still difficult to orient the guide in a correct preoperatively planned location because of the ovular configuration of the deformed acetabulum. Even if the guide is rotated in either a clockwise or counterclockwise orientation while adjacent to the acetabulum, the guide will not necessarily key into the correct preoperatively planned location.

Figure 12:
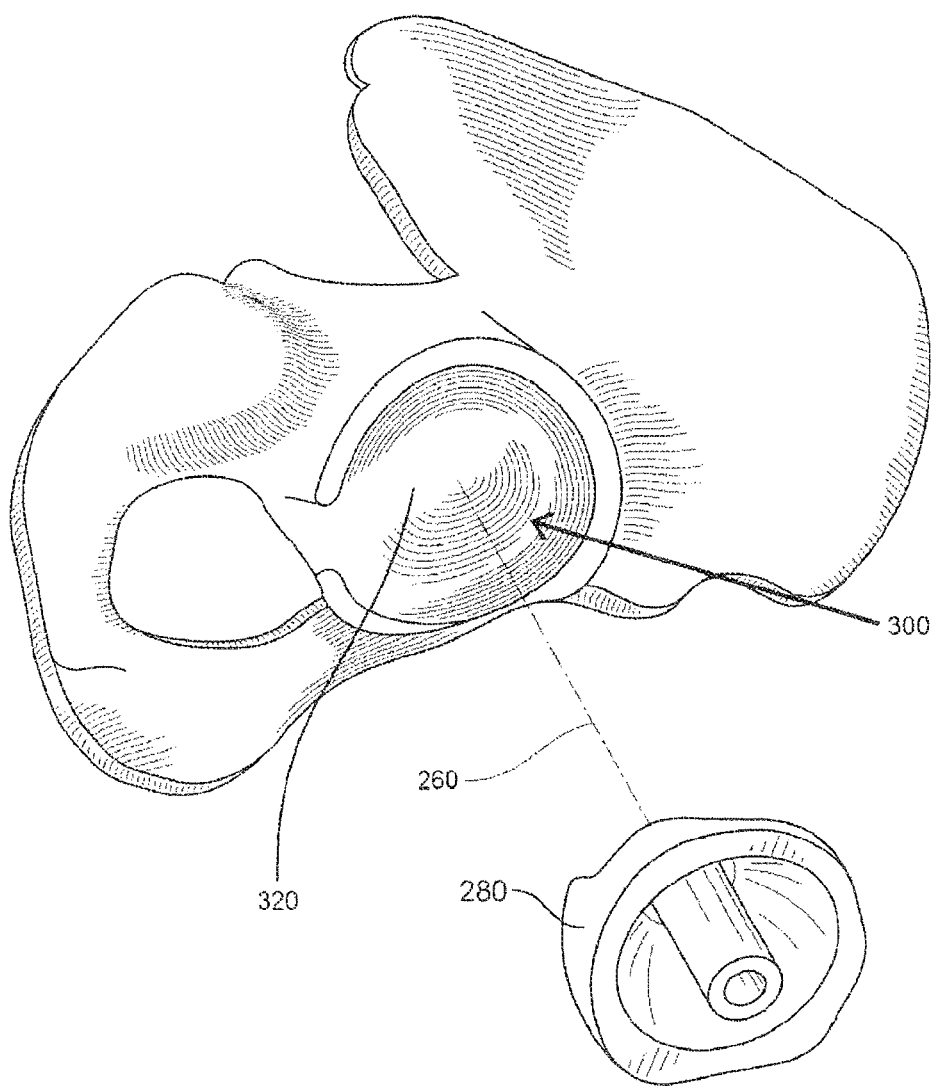
FIG. 12 is an exploded view of a portion of a patient's pelvic region and the guide shown in FIG. 10.
Figure 13:
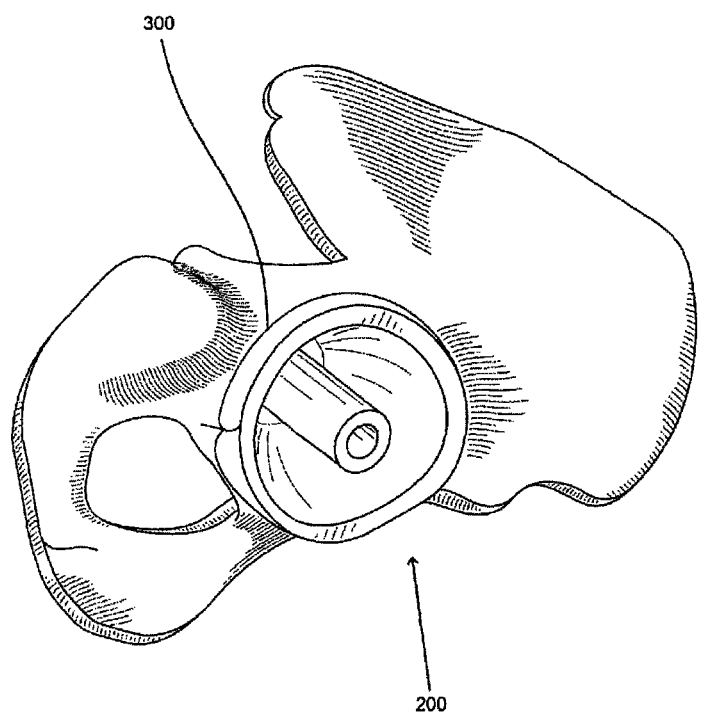
FIG. 13 is an assembled view of the features shown in FIG. 12.

The fovea 340 of the acetabulum is preferably used as an anatomical landmark to easily orient the guide in the correct preoperatively planned position as shown in FIG. 13. Information relating to the location, size and shape of the fovea is analyzed in the preoperative images taken of the acetabulum. This information is used in order to create the patient-specific contact surface of the guide having a feature such as a nub portion or protrusion 280 as shown in FIG. 12 on the contact surface of the guide representing the negative of the fovea shown in FIG. 9.

Figure 11:
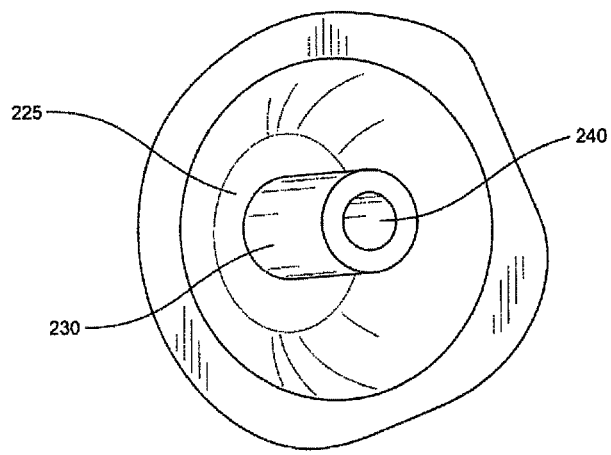
FIG. 11 is another perspective view of the guide shown in FIG. 10.

Guide 200 further includes a guide portion 230 extending outwardly from an inferior surface 225 of guide 200. Guide portion 230 has a guide slot 240 therethrough as shown in FIG. 11. Guide slot 240 has an axis 260 representing an insertional vector of an acetabular component. During the preoperative planning of the guide, accurate acetabular component placement is generally first determined. The polar axis of the acetabular component in the accurately placed or implanted location and orientation is preferably co-linear with the axis of the guide slot.

Figure 14A:
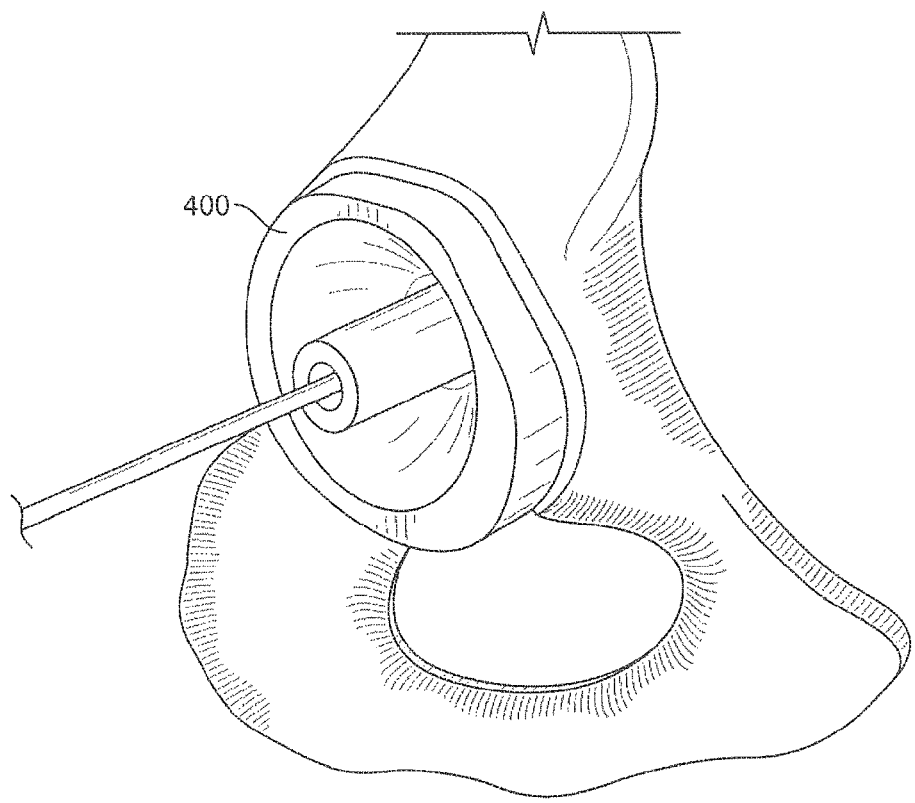
FIG. 14A is a view of a navigated pointer inserted into a guide slot of a patient-specific guide.

Once the optimal location of the acetabular component is determined in order, for example, to correct a patient's deformity, the location and orientation of the guide slot of the guide may then be determined. The guide slot of the guide is adapted to receive means for resecting bone as shown in FIG. 14A. The bone resection means may be a rotating drill, for example. Once the guide is correctly positioned, a drill may be used to resect a portion of bone and/or cartilage of the acetabulum. After a portion of the bone and/or cartilage of the acetabulum are removed, the guide may then be removed. A guide recess formed by the resection, the recess having an axis co-linear with the polar axis of a correct placed acetabular component is now located in the bone of the acetabulum. This guide recess is used to accurately locate a cutting tool such as a reamer as shown in FIG. 14C, for example, used to remove a sufficient amount of the bone of the acetabulum in order to repair the contact surface for the acetabular component that will be engaged thereto. After the acetabulum is reamed, the acetabular component is accurately implanted in the acetabulum and affixed thereto with a fastening means such as a screw, for example. The screw is positioned through a hole in the acetabular component and into the guide recess previously formed by the guide slot of the guide. A longitudinal axis of the hole is co-linear with the polar axis of the accurately positioned acetabular component.

Figure 14B:
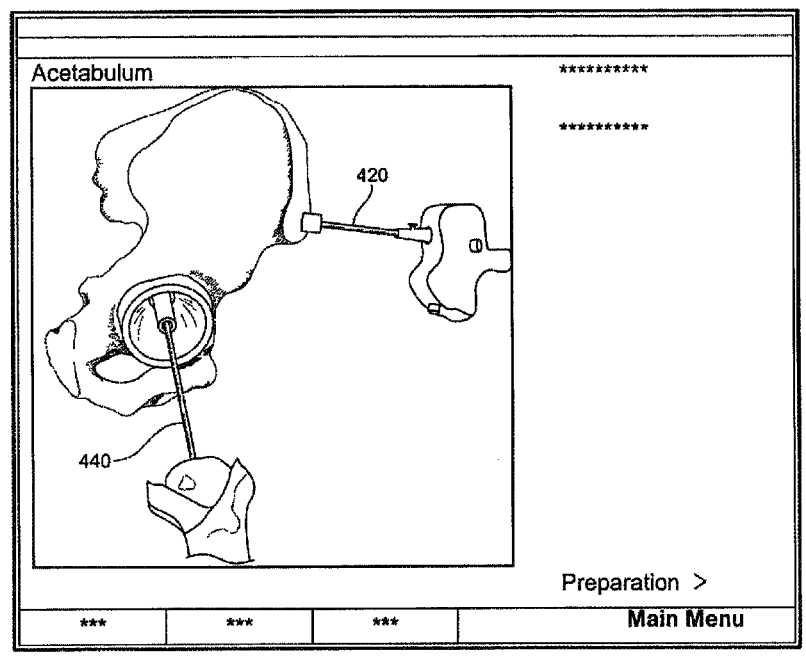
FIG. 14B is a view of a navigation system registering the orientation and location including depth of the pointer shown in FIG. 14A relative to a global coordinate system created by trackers.
Figure 14C:
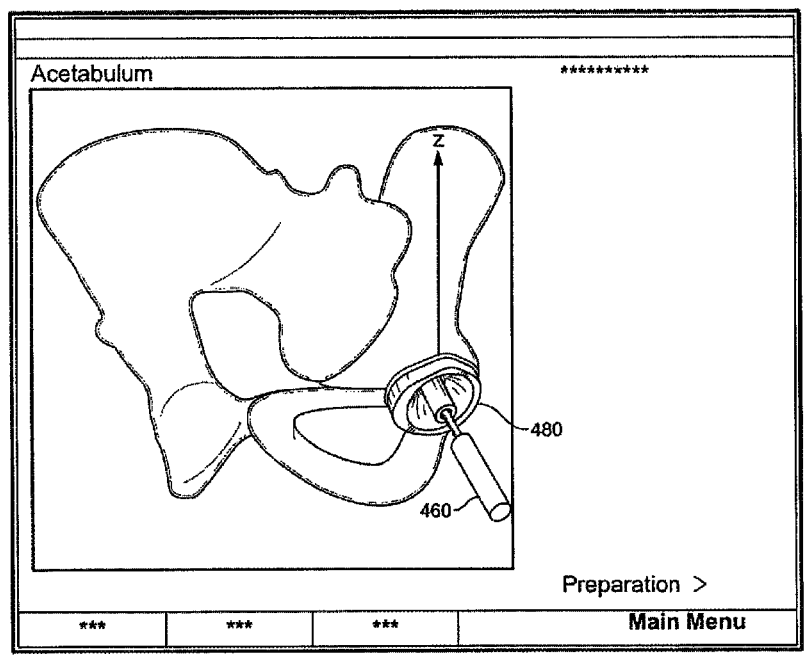
FIG. 14C is a view of a navigated reamer handle and navigated cup inserter being used to prepare the acetabulum in the correct orientation based on the registered target.

FIGS. 14A-C also depict a method of using a patient-specific guide 400 in conjunction with a navigation system for preparation and positioning of an acetabular component. Preoperative images of a patient's pelvic region are taken using CT, MRI or other imaging methodology. The images are evaluated to determine the correct axis of orientation for the acetabular cup to achieve optimal range of motion for a femoral component and maximum acetabular body coverage while minimizing the reaction forces experienced in the acetabular cup. The image data is manipulated to create a patient-specific 3D model guide as shown in FIG. 14A depicting the unique negative impression of the contour of the acetabulum with a guide slot having an axis incorporated as a feature in the model. The patient-specific guide may then be manufactured.

Intraoperatively, a patient is prepared in a standard manner for a navigated total hip arthroplasty procedure. Tracker pins 420 are placed in the iliac crest or other rigid area of the acetabulum. Incision is made and femoral neck is resected. The patient-specific guide is then placed into the acetabulum. As shown in FIG. 14B, a navigated pointer 440 is inserted into the guide slot or is alternatively aligned with the prescribed axis. The navigation system registers the exact orientation and location including depth of the pointer relative to a global coordinate system created by the trackers. The patient-specific guide may then be removed from the acetabulum. As shown in FIG. 14C, a navigated reamer handle 460 and then navigated cup inserter 480 are used to prepare the acetabulum in the correct orientation based on the registered target.

The guide of the present invention may also be created without the use of preoperative imaging. While the exact configuration of the acetabulum of each individual is unique, the size and shape of the acetabulum of an individual generally falls within a range of sizes and shapes. Therefore, a guide selected from a set of differently sized guides may be used on a certain individual during a hip arthroplasty procedure. Each of the guides may also include a guide slot having an axis representing the insertional vector of a corresponding acetabular component. The insertional vector and/or contact surface of the guide may be determined through antroprometric data of the acetabulum.

Figure 15:
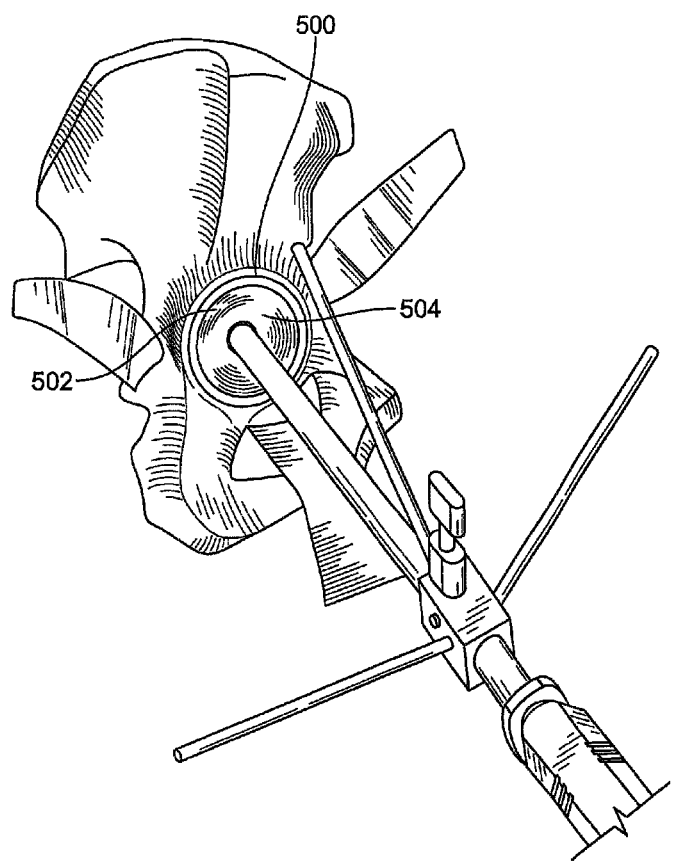
FIG. 15 is a view of one embodiment of an acetabular component of the present invention having apertures through an outer circumference thereof.

FIG. 15 shows an acetabular component, implant or cup 500 configured with apertures 502 oriented about an outer circumference 504 of the cup for screw fixation. The cup shown includes apertures having a location that is preoperatively determined. The location of the screws holes can be preoperatively determined such that after the acetabular cup is implanted in a predefined position within the acetabulum, the apertures are located in a position wherein fixation means such as screws or the like can secure the cup to the acetabulum without impinging on certain neurovascular structures. Also, the angles that the screws are inserted can also be preoperatively determined based on the anatomy of the patient.

Generally, the longer the screw, the more precisely it must be placed. If the acetabular cup is maloriented, then the apertures or holes are generally not in the proper position to insert the screws safely. The acetabular cup shown allows for proper rotational alignment of the cup so that the holes are in a preferred position to insert screws safely into the pelvis without injury to neurovascular structures.

Figure 16A:
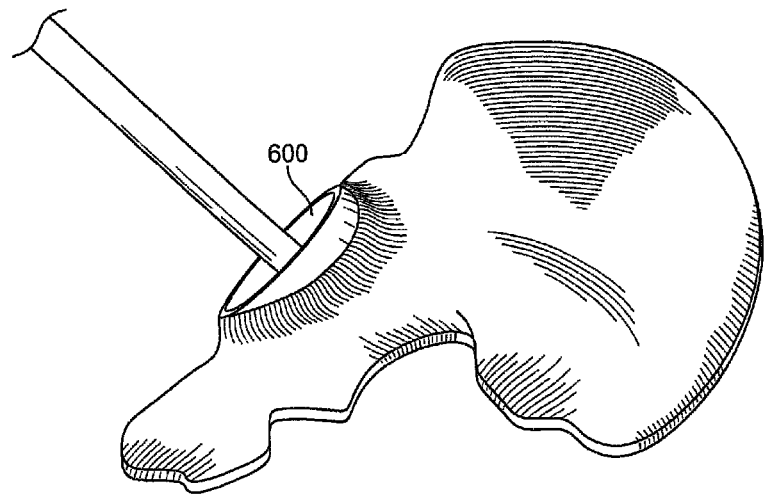
FIG. 16A is a view of one embodiment of a patient-specific guide positioned in an acetabulum of a patient.
Figure 16B:
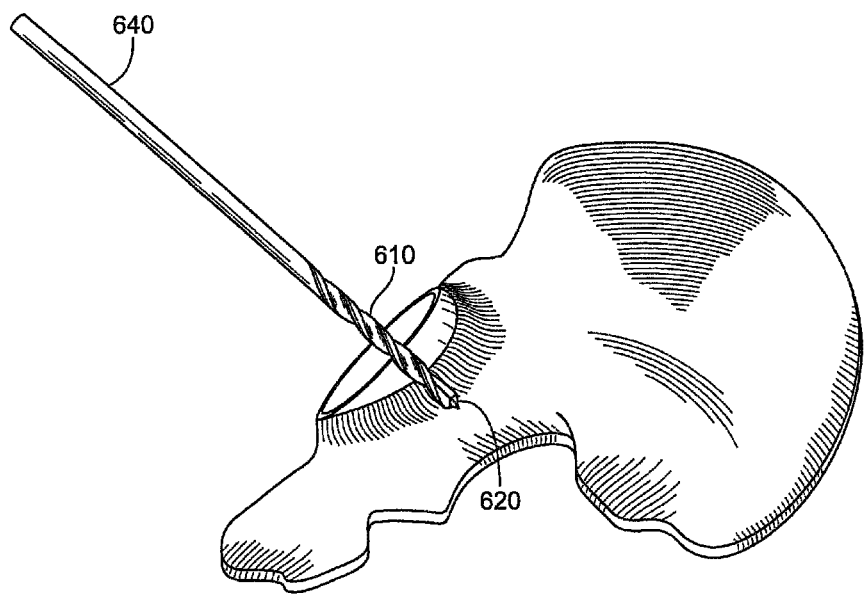
FIG. 16B is a view of the patient-specific guide shown in FIG. 16A wherein a guide pin is positioned through a guide slot of the patient-specific guide.

FIGS. 16A-C show, in part, one method of the present invention. As shown in FIG. 16A, patient-specific guide component 600 is positioned within an acetabulum of a patient. Preferably, guide 600 is rotated about the acetabulum of the patient until a nub portion of the patient-specific guide is received by and is engaged to the fovea of the acetabulum of the patient.

As shown in FIG. 16B, after the patient-specific guide has been correctly positioned on the acetabulum, a guide recess 620 is created in the acetabulum of the patient. Guide recess 620 is preferably created by guiding a guide pin 640 through a guide slot 610 of a guide portion of the patient-specific guide and into the acetabulum of the patient a desired distance from an articular surface of the acetabulum.

FIG. 16C shows patient-specific guide 600 being removed from the guide pin 640 located in the acetabulum and a cannulated reamer 650 placed over guide pin 640. Cannulated reamer preferably rotates about guide pin 640 while translating in a proximal direction in order to resect the articular surface of the acetabulum. Preferably, reamer 650 resects the acetabulum until the reamer travels in the proximal direction the desired distance. In some instances, reamer 650 may travel in the proximal direction more or less than the desired distance based on decisions made by the surgeon.

After resecting the acetabulum with reamer 650, the reamer and guide pin 650 are removed and an acetabular implant is preferably implanted in the resected acetabulum. Preferably, the acetabular implant has a polar axis coaxial with a longitudinal axis of the guide recess created in the acetabulum by the guide pin.

Figure 17:
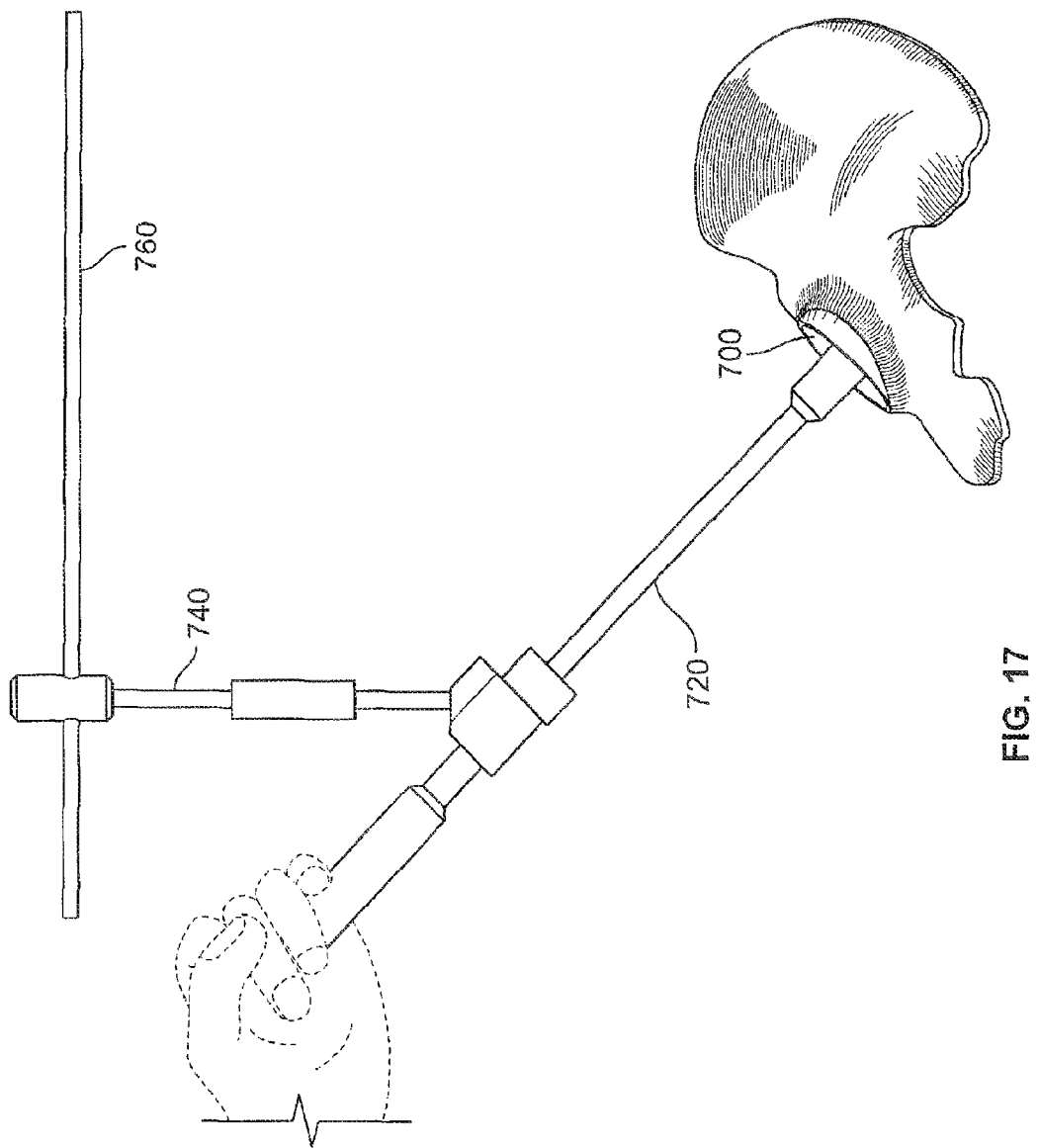
FIG. 17 is a view of one embodiment of an electronic device used to record the position of a patient-specific guide positioned in an acetabulum of a patient.

FIG. 17 shows one embodiment of an electronic device 760 used to record the position of a patient-specific guide 700 positioned in an acetabulum of a patient. This embodiment, uses Global Positioning System ("GPS") or like technology to capture the position of guide 700 such that this information may be used to recreate the position of an insertional vector, for instance, on trials and implants later on.

Once guide 700 is correctly positioned in the acetabulum, an electronic measurement may be taken by electronic device 760 of the exact insertional vector or angle in space defined by a guide slot in guide 700, for example. This measurement or "snapshot" preferably serves as a baseline orientation and can be used in subsequent steps, e.g., reaming and acetabular component insertion, in order to reproduce the insertional angle derived from guide 700.

The value of this measurement comes in the fact that once reaming of the acetabulum begins, guide 700 will no longer fit into the acetabulum in its preoperatively planned position and therefore can no longer serve as a reference for orientation. This technology may be incorporated into a personal digital assistant ("PDA") such as the iPhone, for instance. In one embodiment, an application for use with a PDA may be used to measure the insertional vector in space as described above. As shown in FIG. 17, once electronic device 760 is attached to the a guide inserter 720 via an extension element 740, the position of the insertional angle may be set. During reaming and cup insertion, an iPhone (or other similar PDA device) is attached to a reamer handle or cup inserter 720 and the insertional angle is remeasured. At this point, the reamer handle or cup inserter position can be readjusted to match the original position which was set by guide 700.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A patient-specific guide comprising:
   a superior surface shaped to substantially match a socket joint of a patient;
   an extension portion projecting outwardly from the superior surface to stabilize the patient-specific guide in the socket joint; and
   a guide portion extending outwardly from an inferior surface, the guide portion having an aperture with a longitudinal axis that aligns with a rotational axis of a corresponding joint component,
   wherein the extension portion is shaped to substantially match the shape of anatomical features of the socket joint adjacent a rim of the socket joint, and
   wherein the extension portion is shaped such that when the extension portion engages the anatomical features, the guide is located in a preoperatively planned position and orientation with respect to the socket joint and is shaped such that the guide may be rotated about the socket joint until being received in a recess adjacent a periphery of the socket joint to confirm the preoperatively planned position and orientation.

2. The guide of claim 1, wherein the superior surface is generally convex.

3. The guide of claim 2, wherein the extension portion is generally convex and has a greater convexity in at least one direction than that of the superior surface.

4. The guide of claim 1, further comprising a planar end surface intermediate the superior and inferior surfaces thereof.

5. The guide of claim 4, wherein the guide portion extends outwardly from the inferior surface such that at least a portion thereof is located distally of a plane defined by the planar end surface.

6. The guide of claim 1, wherein the guide portion has inner and outer wall surfaces and a distal end surface intermediate the inner and outer surfaces thereof.

7. The guide of claim 6, wherein the distal end surface of the guide portion is planar.

8. The guide of claim 1, wherein the guide portion is cylindrically shaped.

9. The guide of claim 1, wherein the inferior surface of the guide is generally concave.

10. A patient-specific guide comprising:
- a generally convex superior surface shaped to substantially match a socket joint of a patient;
- a generally convex extension portion projecting outwardly from the superior surface to stabilize the patient-specific guide in the socket joint, the extension portion having a greater convexity in at least one direction than that of the superior surface; and
- a guide portion extending outwardly from an inferior surface, the guide portion having an outer wall and an inner wall, the inner wall forming a slot having a longitudinal axis that aligns with a rotational axis of a corresponding joint component, wherein the extension portion is shaped to substantially match the shape of anatomical features of the socket joint adjacent a rim of the socket joint, and wherein the extension portion is shaped such that when the extension portion engages the anatomical features, the guide is located in a preoperatively planned position and orientation with respect to the socket joint.

11. The guide of claim 10, wherein the extension portion is shaped such that the guide may be rotated about the socket joint until being received in a recess adjacent a periphery of the socket joint to confirm the preoperatively planned position and orientation.

12. The guide of claim 10, further comprising a planar end surface intermediate the superior and inferior surfaces thereof.

13. The guide of claim 12, wherein the guide portion extends outwardly from the inferior surface such that at least a portion thereof is located distally of a plane defined by the planar end surface.

14. The guide of claim 10, wherein the guide portion has inner and outer wall surfaces and a distal end surface intermediate the inner and outer surfaces thereof.

15. The guide of claim 14, wherein the distal end surface of the guide portion is planar.

16. The guide of claim 10, wherein the guide portion is cylindrically shaped.

17. The guide of claim 10, wherein the inferior surface of the guide is generally concave.

* * * * *